United States Patent [19]
Barefoot et al.

[11] Patent Number: 5,639,659
[45] Date of Patent: Jun. 17, 1997

[54] **PROCESS FOR INHIBITING THE GROWTH OF BACTERIA USING BACTERIOCINS PRODUCED BY *PROPIONIBACTERIUM JENSENII* STRAIN ATCC 4872**

[75] Inventors: Susan F. Barefoot, Liberty, S.C.; Dale A. Grinstead, Waterloo, Iowa

[73] Assignee: Clemson University, Clemson, S.C.

[21] Appl. No.: 249,085

[22] Filed: May 25, 1994

Related U.S. Application Data

[63] Continuation of Ser. No. 997,941, Dec. 29, 1992, abandoned.

[51] Int. Cl.$^6$ .................... C12N 1/20; C12P 1/00
[52] U.S. Cl. ............ 435/252.1; 424/93.1; 424/93.3; 424/93.42; 424/93.43; 426/56; 426/61; 435/42; 435/170; 435/252.9; 435/253.4
[58] Field of Search ............... 435/42, 170, 252.1, 435/252.9, 253.4; 424/93 D, 93 H, 93 J, 93.1, 93.3, 93.42, 93.43; 426/56, 61

[56] References Cited

U.S. PATENT DOCUMENTS

| | | | |
|---|---|---|---|
| 5,026,647 | 6/1991 | Tomes et al. | 435/244 |
| 5,096,718 | 3/1992 | Ayres et al. | 426/9 |

OTHER PUBLICATIONS

Geis et al., "Potential of Lactic Streptococci to Prod. Bacteriocin", Jan. 1983, pp. 205–211.

Grinstead et al. (1992) Applied & Env. Microb., 58, 215–220.

Grinstead et al. (1991) Abst. Gen Meet. Soc. 91, 263.

Rehberger et al, (1990) Appl. & Env. Microb., 56, 864–831.

Abstracts of the 89th Annual Meeting of the American Society of Microbiology New Orleans, LA., May 14–18, 1989.

Thesis, The Detection of Bacteriophage and Bacteriocins Among the Classical Propionibacteria, Dale A. Grinstead, Ames, Iowa 1989.

American Society for Microbiology, Myrtle Beach, SC Nov. 16–18, 1990.

*Primary Examiner*—Michael G. Wityshyn
*Assistant Examiner*—Deborah Ware
*Attorney, Agent, or Firm*—Dority & Manning, P.A.

[57] ABSTRACT

An anti-bacterial agent for controlling the growth of certain lactic acid bacteria is provided. The anti-bacterial agent, or bacteriocin, is produced by *Propionibacterium jensenii*, and specifically by the P126 and P1264 strains of the particular species. The process employs the bacteriocins to inhibit the growth of other bacterial cultures, including yogurt starter cultures. The bacteriocins are stable across a broad range of pHs and are stable at relatively high and prolonged temperatures and have a wide activity spectrum against bacteria. The bacteriocins are particularly useful in controlling the over-acidification of yogurt to decrease the sour taste often found in yogurt.

15 Claims, 1 Drawing Sheet

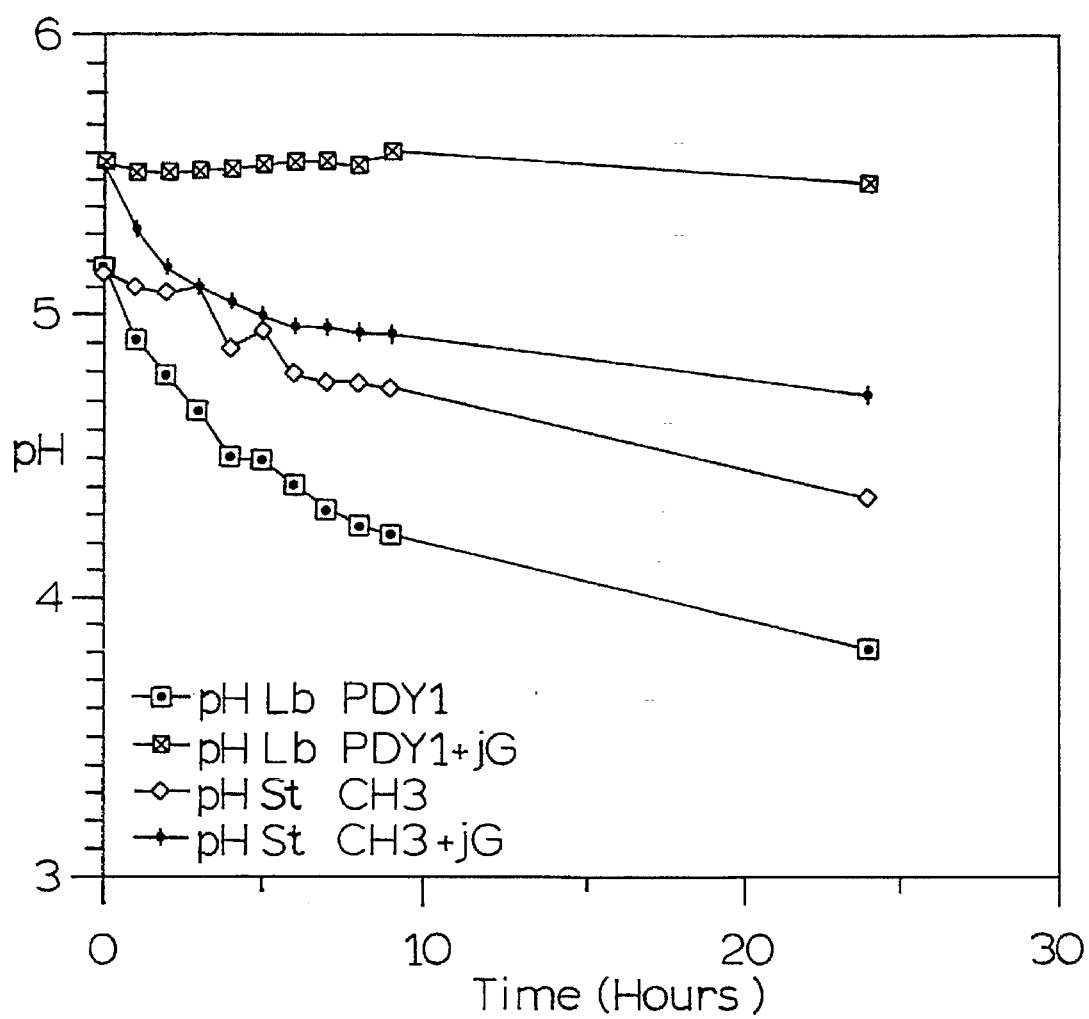
pH of Lb PDY1, LbPDY1+jG, St CH3, St CH3 +jG in Skim Milk ns filed Dec. 29, 1992, which was abandoned upon the filing

PROCESS FOR INHIBITING THE GROWTH OF BACTERIA USING BACTERIOCINS PRODUCED BY *PROPIONIBACTERIUM JENSENII* STRAIN ATCC 4872

This is a continuation of application Ser. No. 07/997,941, filed Dec. 29, 1992, which was abandoned upon the filing hereof.

FIELD OF THE INVENTION

An agent for controlling the growth of bacteria cultures and methods therefor and, particularly, the use of a bactericidal protein to control the growth of bacteria cultures such as those used in making yogurt are provided.

BACKGROUND OF THE INVENTION

Various types of bacteria assist in transforming milk into other foods. In particular, acid-forming bacteria are used in processes for making yogurt, cheeses, buttermilk, sour cream, and other fermented dairy products. Controlling the growth of the bacteria used in producing such foods is important for ensuring edibility and flavor, as well as for preventing excessive curdling and the occurrence of undesirable secondary fermentations.

The present invention is directed to various agents for controlling the growth of bacteria. The anti-bacterial agents described herein are bacterially produced proteins known as "bacteriocins". Bacteriocins are generally defined by three criteria—(1) they are proteins or a complex of proteins; (2) they are active against bacteria closely related to the producer bacterium; and (3) they kill sensitive bacteria by some means other than lysis.

Bacteriocins were first reported in 1925. Filtrates of a particular strain of *E. coli* were observed to strongly inhibit the growth of another strain of *E. coli*. The inhibitory substance was found to be heat-resistant, diffusible through cellophane membranes, and not antigenic. Various other bacteriocins have also been reported in many other gram-positive and gram-negative species.

Bacteriocins are generally divided into two groups: (1) the "true" bacteriocins; and (2) the bacteriophage-like bacteriocins. True bacteriocins lack a complex structure and have an upper limit molecular weight of 400,000 daltons. The true bacteriocins are distinguishable from bacteriophage-like bacteriocins by electron microscopy analysis, during which they appear to be spherical particles ranging from 8 nanometers to 64 nanometers in diameter.

Bacteriophage-like bacteriocins are generally classified into three main groups: (1) tailed particles with full or empty heads that resemble ordinary bacteriophages of Bradley groups A1, B1, B2, or C1; (2) "killer particles" that have small heads and long contractile tails and contain bacterial DNA; and (3) bacteriophage tails that may or may not be contractile. True bacteriophages are viral organisms that destroy bacteria by disintegration and dissolution (lysis).

The nomenclature of bacteriocins is based on the specific name of the host organism. Thus, bacteriocins of *E. coli* are colicins, *Listeria monocytogenes* strains produce monocins, and *Bacillus cereus* strains produce cerecins.

The bacteria genus Propionibacterium, from which the presently described bacteriocins are produced, includes gram-positive nonsporeforming pleomorphic rods. The propionibacteria are nonmotile, have clumps that resemble "Chinese characters" produce large amounts of propionic and acetic acids as fermentation products, are generally catalase-positive, and grow best under anearobic conditions from about 30° C. to 37° C. There are two major groups in the genus Propionibacterium: (1) the acnes group or cutaneous strains; and (2) the classical or dairy strains.

The acnes strains are typically found on human skin. They were originally included in the genus Corynebacterium but were transferred to the genus Propionibacterium because they were anaerobic, produced propionic acid as a major end product of metabolism, contained L-diaminopimellic acid in their peptidoglycan, produced $C_{15}$ iso- and anteiso-acids in cell lipids, and lacked mycolic acids and arabinoglycan, which are characteristics of Corynebacterium. The acnes strains include *P. acnes, P. avidum, P. granulosum*, and *P. lymphophilum*.

Classical species include *Propionibacterium jensenii, P. acidipropionici, E. freudenreichii* subspecies *freudenreichii* and *shermanii*, and *P. thoenii*. These classical species are extremely useful organisms in the food industry and are found in dairy fermentations, other natural fermentations such as silage and olives, and soil. During fermentative metabolism, they convert glucose and lactate to propionate, acetate, and carbon dioxide. The inhibitory effects of propionate and acetate are potentiated by the low pH encountered in Swiss cheese and other fermented products. The major use of such classical propionibacteria is in the production of Swiss cheese, where production of carbon dioxide, propionate and acetate by *Propionibacterium shermanii* (in conjunction with *Streptococcus thermophilus* and *Lactobacillus bulgaricus*) contributes the characteristic flavor, texture, and "eyes" of Swiss cheese.

The propionibacteria also produce large amounts of propionic acid which is used for grain preservation, making of cellulose plastics, and in herbicides. In addition, propionic acid and its salts are incorporated into bakery products to prevent mold growth and ropiness. Although the vast majority of propionic acid in the United States is produced by chemical synthesis, research is underway to improve the economics of propionic acid production by fermentation.

Another industrial product of propionibacteria is Microgard™ made by Wesman Foods, Inc., of Beaverton, Ore. Microgard™ is an FDA-approved and patented product produced by fermenting grade A skim milk with *Propionibacterium shermanii* followed by pasteurizing. Microgard™ is a small heat-stable molecule having a size of about 700 daltons and is antagonistic to most gram-negative bacteria, as well as some yeasts and molds, but not to gram-positive bacteria. It is used as a preservative in about 30% of the cottage cheese produced in the United States. Like propionic acid, Microgard™ inhibits most gram-negative bacteria and some fungi.

The Lactobacillus and Streptococcus genera also include important industrial organisms, particularly for the dairy fermentation industry. Bacteriocins produced by lactobacilli were first identified in 1961. One bacteriocin, lactacin B, is produced by *Lactobacillus acidophilus* N2. This bacteriocin was originally isolated as a 100,000 dalton protein complex that demonstrates bactericidal, but not bacteriolytic (bacteria dissolution) activity, against sensitive cells. The lactacin B complex dissociates to a 6,500-dalton peptide that is responsible for activity. Another bacteriocin produced by *Lactobacillus helveticus* 481 is helveticin J. This bacteriocin is sensitive to proteases and heat (30 min at 100° C.), has a molecular weight of 300,000 daltons, and is, in its natural form, an aggregate of 37,000-dalton proteins that have bacteriocin activity.

The lactic acid-forming bacteria *Lactobacillus delbrueckii* subsp. *bulgaricus* and *Streptococcus salivarius* subsp. *thermophilus* are used to curdle milk into yogurt. These bacteria have become increasingly significant due to the rise of yogurt consumption in the United States over the past 10 years. Annual U.S. consumption is now approximately 1 billion pounds and the wholesale value for non-frozen yogurt in 1989 was $985 million. Per capita consumption in 1989 was about 4 pounds.

Generally, Americans prefer a less sour-tasting yogurt. The sour taste of yogurt arises from over-acidification caused by the above-mentioned starter bacteria strains employed to produce the yogurt. The desirable pH of yogurt is 4.3 to 4.0. During storage, yogurt bacteria, particularly *Lactobacillus bulgaricus*, continue to acidify yogurt and reduce the pH to well below a pH of 4.0 (sometimes as low as 3.2 to 3.5). One method by which the industry currently addresses the problem is to increase the proportion of *Streptococcus thermophilus* cells and decrease the proportion of *Lactobacillus bulgaricus*. Alternatively, the yogurt may be pasteurized to kill both the lactobacilli and streptococci. However, pasteurized yogurt has an altered flavor and lacks the living lactic and bacteria. Thus some benefits attributable to consuming yogurt that contains living cultures are lost. The need exists for a natural foodgrade organism to control the growth of the yogurt starter bacteria so that a less sour, more palatable yogurt can be obtained.

SUMMARY OF THE INVENTION

It is an object of the present invention to provide an anti-bacterial agent for use in controlling bacteria cultures, and particularly lactic acid bacteria cultures.

It is another object of the present invention to provide an agent for controlling the growth of *Lactobacillus bulgaricus* and *Streptococcus thermophilus*.

It is another object of the present invention to provide a bactericidal protein produced by *Propionibacterium jensenii* for use in controlling lactic acid bacteria.

It is another object of the present invention to provide an agent for preventing the over-acidification of lactic acid-based food.

It is another object of the present invention to provide an agent for controlling over-acidification of yogurt.

It is further another object of the present invention to provide a process for using a bactericidal protein produced by *Propionibacterium jensenii* to inhibit the growth of *Lactobacillus bulgaricus* and *Streptococcus thermophilus*.

Generally speaking, the present invention is directed to an anti-bacterial protein (or bacteriocin) and a process for using the bacteriocin to inhibit other bacteria. Particularly, the bacteriocin is produced by *Propionibacterium jensenii*, and more particularly by strain P126 and strain P1264 of that particular species. The process specifically employs bacteriocins obtained from *P. jensenii* P126 and *P. jensenii* P1264 to inhibit the growth of other bacterial cultures, including yogurt starter cultures. The bacteriocins are stable across a broad range of pHs and are stable at relatively high and prolonged temperatures. This stability, coupled with its activity spectrum against certain bacteria and its production by a food grade organism that is already widely used to produce food, makes the bacteriocin of the present invention a highly effective and desirous agent for controlling growth of bacteria cultures such as yogurt.

BRIEF DESCRIPTION OF THE DRAWING

FIG. 1 refers to the pH of Lb PDY1, LbPDY1 +G, St CH3 +G in skim.

DESCRIPTION OF PREFERRED EMBODIMENT

Broadly speaking, the inhibitors produced by *Propionibacterium jensenii* have been found to inhibit the growth of various other strains of bacteria, particularly the lactic acid bacteria. The bacteriocin produced by *Propionibacterium jensenii* strains P126 (ATCC 4872) and P1264 are active against several lactobocilli, including *Lactobacillus bulgaricus* NCDO 1750 and *Lactobacillus delbreckii* subsp. *lactis* ATCC 4797, and against other yogurt cultures such as *Streptococcus salivarius* subsp. *thermophilus*. As taught by the present invention, such activity allows use of the bacteriocin produced by these propionibacteria for controlling the growth of a variety of yogurt cultures in synthetic media and milk so that the over-acidification of yogurt may be prevented and controlled. Because the bacteriocin of the present invention is produced by a foodgrade organism and demonstrates stability to freezing, storage at 4° C. for three days, and heating to 100° C. for two minutes, the present bacteriocin is particularly suited for use in the food industry.

The present invention may be readily understood by reference to the following examples wherein the inhibitory activity of *P. jensenii* bacteriocins on various bacteria, including the bacteria responsible for Swiss cheese and yogurt growth, are indicated.

The inhibitory activity of the bacteriocin produced by the *P. jensenii* P126 strain of Propionibacterium was tested on the various indicator cultures listed on Table 1 and Table 2. The producer culture *P. jensenii* P126, the sensitive indicator *P. acidipropionici* P5, and other indicator propionibacteria were obtained from B. A. Glatz (Iowa State University Department of Food and Human Nutrition, Ames). The P1264 strain of *P. jensenii* was obtained from the All-Union Collection of Microorganisms at the USSR Academy of Sciences in Moscow. The remainder of the indicator cultures were obtained from the Clemson University Food Microbiology culture collection.

Propionibacteria were cultured in sodium lactate broth (NLB) that consisted of 1% Trypticase soy broth without dextrose obtained from BBL Microbiology Systems of Cockeysville, Md., 1% yeast extract obtained from Difco Laboratories of Detroit, Mich., and 1% sodium lactate syrup (60%) obtained from Fisher Scientific Co. of Pittsburg, Pa. in distilled water. Sodium lactate agar (NLA) was prepared from NLB by adding 1.8% agar obtained from BBL and soft NLA was prepared by the addition of 0.7% agar.

Growth conditions for the indicator organisms employed herein are described in Tables 1 and 2. Stock cultures of *Clostridium perfringens* were maintained at room temperature in cooked-meat medium obtained from Difco. Molds were stored at room temperature on potato dextrose agar plates obtained from Difco. All other cultures were maintained in the appropriate growth medium containing 10% glycerol and stored at −70° C. All cultures were propagated twice in the appropriate medium and examined for purity by being streaked for isolation prior to experimentation. Gram stains and growth characteristics were used to confirm the identity of propionibacterial cultures.

Inhibitory activity was detected by two techniques: (1) the deferred method; and (2) the agar plug method. With the deferred method, the producer culture was spot inoculated to the center of NLA plates and held at 37° C. under anaerobiosis for 7 to 10 days using a BBL GasPak. Each plate was overlaid with tempered soft agar seeded with $10^4$ to $10^5$ cells of *P. acidipropionici* P5 or other appropriate indicator. Plates were then held under conditions optimal for growth of the indicator bacteria and observed for inhibition of the indicator lawn after 24 and 48 hours.

The agar plug method was used to eliminate the effects of growing cells. Using this method, NLA plates were spot inoculated with P. jensenii P126 and held for 7 to 10 days anaerobically or under flowing $CO_2$ (0.4 liter/hour) at 32° C. One centimeter diameter plugs were cut from NLA agar next to the producer colonies. Agar plugs were transferred aseptically to wells in a sterile medium and overlaid with a soft agar lawn of indicator cells, incubated appropriately, and observed for zones of inhibition.

TABLE 1

Effect of bacteriocin produced by Propionibacterium jensenii P126 on selected indicator cultures[a]

| Indicator organism | Sensitivity to bacteriocin produced by Propionibacterium jensenii P126[b] | Culture conditions Temp (°C.) | Medium[c] |
|---|---|---|---|
| Aspergillus carneus | – | 25 | PDA |
| Aspergillus niger | – | 25 | PDA |
| Aspergillus terreus | – | 25 | PDA |
| Cladiosporum sp. | – | 25 | PDA |
| Discula sp. | – | 25 | PDA |
| Penicillium sp. | – | 25 | PDA |
| Penicillium italicum | – | 25 | PDA |
| Ulodadium sp. | – | 25 | PDA |
| Bacillus cereus ATCC 232 | – | 37 | BHI |
| Clostridium perfringens ATCC 3624 | – | 37 | FTG[d] |
| Citrobacter freundii ATCC 8090 | – | 37 | BHI |
| Enterobacter aerogenes ATCC 13048 | – | 37 | BHI |
| Enterobacter cloacae ATCC 23355 | – | 37 | BHI |
| Enterococcus faecalis ATCC 19433 | – | 37 | M17 |
| Escherichia coli ATCC 25922 | – | 37 | BHI |
| Escherichia coli O:24 B:17 | – | 37 | BHI |
| Klebsiella pneumoniae ATCC 13883 | – | 37 | BHI |
| Listeria grayi ATCC 19120 | – | 37 | BHI |
| Listeria innocua ATCC 33090 | – | 37 | BHI |
| Listeria monocytogenes | – | 37 | BHI |
| Listeria murrayi ATCC 25402 | – | 37 | BHI |
| Pseudomonas aeruginosa ATCC 27853 | – | 37 | BHI |
| Salmonella typhimurium ATCC 14028 | – | 37 | BHI |
| Seratia marcescens ATCC 8100 | – | 37 | BHI |
| Shigella flexneri ATCC 12022 | – | 37 | BHI |
| Shigella sonnei ATCC 25931 | – | 37 | BHI |
| Staphylococcus aureus ATCC 25923 | – | 37 | BHI |
| Staphylococcus epidermidis ATCC 12228 | – | 37 | BHI |

[a]Indicator cultures other than propionibacteria were incubated for 18 h prior to preparation of the lawn.
[b]Sensitivity (+) or insensitivity (–) of cultures to bacteriocin produced by Propionibacterium jensenii P126 was determined by both deferred and agar plug assay methods.
[c]PDA, potato dextrose agar; BHI, brain heart infusion; FTG, fluid thioglycolate; M17, M-17 broth with 1% lactose. All media were obtained from Difco Laboratories.
[d]Broth cultures of C. perfringens were incubated in tightly closed screw-capped tubes.

TABLE 2

Effect of bacteriocins produced by Propionibacterium jensenii P126 on selected lactic and propionic acid bacteria[a]

| Indicator organism | Sensitivity to bacteriocins produced by Propionibacterium jensenii P126[b] | Culture conditions Temp (°C.) | Medium[d] |
|---|---|---|---|
| Lactobacillus | | | |
| acidophilus ATCC 6032 | – | 37 | MRS |
| acidophilus N2 | – | 37 | MRS |
| bulgaricus NCDO 1489 | + | 37 | MRS |
| casei ATCC 7469 | – | 37 | MRS |
| delbrueckii subsp. lactis ATCC 4797 | + | 37 | MRS |
| fermentum NCDO 1750 | – | 37 | MRS |
| helveticus NCDO 87 | + | 37 | MRS |
| lactis NCDO 970 | – | 37 | MRS |
| plantarum NCDO 1752 | – | 37 | MRS |
| viridescens ATCC 12706 | – | 37 | MRS |
| Lactococcus | | | |
| lactis subsp. cremoris NCDO 799 | + | 32 | M17 |
| lactis subsp. lactis C2 | + | 32 | M17 |
| Propionibacterium | | | |
| acidipropionici P5 | + | 32 | NLB |
| freudenreichii subsp. shermanii P38 | – | 32 | NLB |
| jensenii P54 | + | 32 | NLB |
| jensenii P63 | – | 32 | NLB |
| freudenreichii subsp. shermanii P93 | – | 32 | NLB |
| freudenreichii subsp. shermanii P100 | – | 32 | NLB |
| freudenreichii subsp. freudenreichii P103 | – | 32 | NLB |
| jensenii P126 | – | 32 | NLB |
| thoenii P127 | – | 32 | NLB |

[a]Indicator cultures other than propionibacteria were incubated for 18 h prior to preparation of the lawn. Propionibacteria were held for 24 h.
[b]Sensitivity (+) or insensitivity (–) of cultures to bacteriocins produced by Propionibacterium jensenii P126 was determined by both deferred and agar plug assay methods.
[c]All cultures were incubated under flowing $CO_2$ (0.4 liter/h).
[d]MRS, lactobacillus MRS broth (BBL); M17, M-17 broth with 1% lactose (Difco); NLB, sodium lactate broth.

EXAMPLE 1

One particular bacteriocin of the present invention was prepared by two methods. In the method described in this Example 1, agar extracts containing activity were prepared by initially spot inoculating P. jensenii P126 to the surface of soft NLA and incubating the culture at 32° C. for 7 to 10 days under anaerobiosis. Producer colonies were removed with a sterile cork borer and discarded. The remaining agar was aseptically transferred to a sterile plastic bag, macerated by hand, and frozen overnight at –20° C. The bags were then held at 4° C. for 24 hours to permit diffusion of the inhibitor into the aqueous phase. Agar was removed by centrifugation for 1 hour at 4° C. at 9,000 rpm in a GSA JA-14 rotor made by Beckman of Palo Alto, Calif.

EXAMPLE 2

The bacteriocin produced by Propionibacterium jensenii P126 was then alternatively produced from broth cultures. NLB cultures of P. jensenii P126 were incubated at 32° C. for 10 days under anaerobiosis. Cells were removed by centrifugation according to the method described above. The supernatant was passed sequentially through a 1.2 μm pore-size membrane filter made by Millipore of Bedford, Mass. and a 0.45 μm pore-size filter made by Gelman of Ann Arbor, Mich. The supernatant was then transferred to dialysis tubing with a 10,000- to 12,000-molecular weight cutoff made by Spectrum Medical Industries, Inc. of Los Angeles, Calif., and concentrated to 1/50 to 1/100 of the original volume against polyethylene glycol 3,500 or 20,000 obtained from Sigman. In an alternative method, the supernatant was lyophilized in a freeze drier made by VirTis Inc. of Gardiner, N.Y. and resuspended in 1/50 to 1/100 of the original volume of sterile distilled water. Concentrated supernatant was then dialyzed exhaustively against a 0.1M phosphate buffer having a pH of 6.8.

EXAMPLES 3–4

Activity of the P126 bacteriocin was assayed by two methods. First, the bacteriocin was spotted in 10- to 50-μl portions onto NLA plates containing an indicator lawn ($10^4$ to $10^5$ CFU/ml), dried at 23° C. for 120 minutes, and held at 32° C. for 48 hours. Additional assays were performed by the agar-well diffusion method described by Tagg and McGiven in "Assay System for Bacteriocins", 21 Applied Microbiology 943 (1971), which is incorporated herein by reference in its entirety. The titer of the P126 bacteriocin was defined as the reciprocal of the highest dilution inhibiting the indicator lawn and expressed as activity units (AU) per milliliter.

The *Propionibacterium jensenii* bacteriocin was examined for adsorption to *P. acidipropionici* P5 and *Lactobacillus delbrueckii* subsp. *lactis* ATCC 4797. One milliliter aliquots of overnight cultures of *P. acidipropionici* P5 and *L. delbrueckii* subsp. *lactis* ATCC 4797 were pelleted by centrifugation. The cell pellets were washed twice in a 0.1M phosphate buffer having a pH of 6.8, resuspended in 0.1 ml of the bacteriocin (20 or 1,600 AU/ml against *P. acidipropionici* P5 or *L. delbrueckii* subsp. *lactis* ATCC 4797, respectively), and held at 32° C., 37° C. and 4° C. Replicates were removed at 0, 1, 2, 3, 4, 5, 6, 12, and 24 hours. Cells were removed by centrifugation and filtration through a 0.45 μm pore-size filter, and the bacteriocin activity against *P. acidipropionici* P5 and *L. delbrueckii* subsp. *lactis* ATCC 4797 was determined. Viable cell counts were determined at each interval by standard colony count methods described by Busta, Peterson, Adams and Johnson in "Colony Count Methods", Compendium of Methods for the Microbiological Examination of Foods (2d ed. American Public Health Association), which is incorporated by reference herein in its entirety.

EXAMPLE 5

*P. jensenii* P126 was examined by both the deferred and agar plug methods for inhibition of molds, dairy propionibacteria, selected lactic acid bacteria, and the other gram-positive and gram-negative indicator species shown in Tables 1 and 2. Inhibitory activity of *P. jensenii* P126 was confined to two dairy propionibacteria, *P. jensenii* P54 and *P. acidipropionici* P5, and selected lactic acid bacteria, including *Lactobacillus bulgaricus* NCDO 1489, *Lactobacillus helveticus* NCDO 87, *L. delbrueckii* subsp. *lactis* ATCC 4797 (formerly *Lactobacillus leichmannii*), *Lactococcus lactis* subsp. *cremoris* NCDO 799, and *Lactococcus lactis* subsp. *lactis* C2. The *P. jensenii* P126 bacteriocin did not inhibit itself or any of the other examined strains and was 40 times more active against the lactobacilli than against the most sensitive propionibacteria.

EXAMPLE 6

The effect of selected enzymes on the inhibitory agent produced by *P. jensenii* P126 was then examined. Treatment of inhibitory agar cultures with proteinase K, pronase E, and type 14 protease destroyed antagonistic activity, suggesting that the agent responsible for inhibition was actually a protein and, thus, classifiable as a bacteriocin. Treatment with catalase had no effect, indicating that the inhibitor produced by *P. jensenii* P126 was not $H_2O_2$.

EXAMPLE 7

The temperature sensitivity of the bacteriocin produced by *P. jensenii* P126 was then examined. Inhibitory activity in agar plugs was unaffected by heat treatment for periods of 15, 30, 45, and 60 minutes at 50° C. or for a period of 2 minutes at 100° C. Continued treatments at 5, 10, and 15 minutes at 100° C. resulted in diminished activity. Unlike a bacteriocin produced by *P. thoenii* P127 that also inhibits dairy bacteria but is only stable to 85° C. the P126 bacteriocin is stable to 100° C. for 20 minutes. Activity in agar plugs that had been frozen at −20° C. for 16 to 18 hours was indistinguishable from the bacteriocin's activity in unfrozen agar plugs. Such a wide range of temperature stability allows the P126 bacteriocin to be used in heat-preservable foods. In addition, its long-term storage stability is a major advantage allowing extended shelf life for foods employing the bacteriocin.

EXAMPLE 8

Next, the bacteriocin was characterized according to its activity, concentration and stability to pH. No activity was detected in unconcentrated NLB cultures of *P. jensenii* P126 held at 32° C. for 1 to 10 days. Adjustment of the NLB to pHs of 5.0, 5.5, 6.0, 6.5, 7.0, 7.5, 8.0, 8.5, and 9.0 prior to addition of the *P. jensenii* P126 producer culture (1%) permitted growth but did not result in detectable production of the bacteriocin prior to concentration. During these studies, it was found that the inhibitor of *Propionibacterium jensenii* P126 remained active over a pH range of from 3.0 to 11.0.

Activity was detected only in agar cultures of the producer *P. jensenii* P126 and concentrates (50× to 100×) of spent broth cultures. Producer cultures propagated on NLA, glucose agar (NLA agar containing 0.6% glucose in lieu of sodium lactate), or lactose agar (NLA containing 0.6% lactose instead of sodium lactate) demonstrated activity of the bacteriocin. More activity was detected in 24 hour lactose agar producer cultures than in 24 hour glucose agar or NLA producer cultures. However, continued producer growth on NLA resulted in more activity in 4- and 5-day NLA cultures than in the corresponding lactose or glucose agar cultures. Anaerobic incubation and incubation under flowing $CO_2$ at a rate of 0.4 liter/hour of NLA or lactose agar producer cultures resulted in equivalent production of the particular bacteriocin. Anaerobically-held glucose agar cultures produced more of the bacteriocin than those held under flowing $CO_2$, but not more than NLA producer cultures.

Like the bacteriocin activity in agar plugs, activity in NLA producer culture extracts and concentrated NLB spent producer cultures was sensitive to proteinase K and insensitive to catalase. In addition, the antagonist in culture extracts inhibited the same indicator species as did agar plugs containing the bacteriocin. The availability of the bacteriocin in soluble form permitted its titration against sensitive indicator species. Crude bacteriocin from both sources was more inhibitory to *L. delbrueckii* subsp. *lactis* ATCC 4797 than to *P. acidipropionici* P5. Titers of the same extract against these organisms were 400 and 20 AU/ml, respectively.

The heat and pH stability of the *Propionibacterium jensenii* bacteriocins allow the use of inhibitors in several media, including the acidic yogurt media and others that undergo a heating process such as pasteurization. The typical pasteurization process for yogurt is one minute at 180° F., which is clearly within the range of heat stability exhibited by the bacteriocin.

EXAMPLE 9

As discussed above, bacteriocins typically exhibit bactericidal, rather than bacteriolytic, action. Addition of 20 AU/ml of the P126 bacteriocin to $1.9 \times 10^7$ cells of the sensitive indicator *P. acidipropionici* P5 stopped growth, but did not result in cell death. Addition of lower concentrations, such as 5 to 10 AU/ml, had no effect on indicator cell growth as shown in Table 3. Treatment of *P. acidipropionici* P5 with 20 AU/ml of the bacteriocin for 1, 2, 3, 4, 5, 6, and 12 hours resulted in decreased indicator populations. Exposure of *L. delbrueckii* subsp. *lactis* 4797 to the bacteriocin decreased viable cell numbers by approximately 99%, further indicating a bacteriostatic action for the bacteriocin toward *P. acidipropionici* P5 and a bactericidal mode of action toward *L. delbrueckii* subsp. *lactis* 4797. Microscopic examination of the treated *lactobacilli* revealed only intact cells with no cell fragments or lysed cells detected.

TABLE 3

Effect Of bacteriocins produced by *Propionibacterium jensenii* P126 on *P. acidipropionici* P5[a]

| Activity (AU/ml) | Treatment temp (°C.) | Population (CFU/ml) after 24 h |
|---|---|---|
| 20 | 32 | $1.7 \times 10^7$ |
| 10 | 32 | $>2.5 \times 10^{10}$ |
| 5 | 32 | $>2.5 \times 10^{10}$ |
| 0 | 32 | $>2.5 \times 10^{10}$ |
| 0 | 4 | $3.5 \times 10^7$ |

[a]Crude bacteriocins produced by *Propionibacterium jensenii* P126 was obtained by freezing, thawing, and equilibrating (4° C., overnight) NLA cultures (32° C., 7 to 10 days) of *P. jensenii* P126, decanting the liquid, concentrating it 100-fold by lyophilization, and passing it through a microfilter (0.45 μm pore size) to remove cells. Crude jenseniin G was added to $1.9 \times 10^7$ CFU of *P. acidipropionici* P5 from an NLB culture (24 h, 32° C Exposure of *L. delbrueckii* subsp. *lactis* 4797 to the P126 bacteriocin at 1,600 AU/ml for 24 hours at 4° C. or 37° C. reduced activity to 400 AU/ml. Treatment of *P. acidipropionici* P5 with 20 AU/ml of the bacteriocin under the same conditions resulted in no decrease in activity.

EXAMPLE 10

The P126 bacteriocin was also prepared from NLB cultures of *Propionibacterium jensenii* P126 by incubating the NLB cultures for 10 days at 32° C. under $CO_2$ flowing at 0.4 l/hour. The cultures were centrifuged and filtered to remove the cells. Protein in spent media was precipitated by adding ammonium sulfate to 80%. The samples were then stirred at 4° C. for 1 hour and centrifuged to pellet the protein. The protein was resuspended in ¹⁄₁₀₀ of the original volume of water. The protein content was determined by a Coomassie blue assay of Bio-Rad and the activity was titered. The bacteriocin was further purified by chromatofocusing at two pH ranges of 4 to 7 and 6 to 9. All fractions were examined for inhibitory activity against *L. delbrueckii* subsp. *lactis* and the protein content was determined for those fractions exhibiting activity. The protein content and activities are shown in Table 4.

TABLE 4

| Sample | Au/l | Total activity | Protein (mg/ml) | total Protein | Specific activity (AU/ml) | Fold Purification | Yield % |
|---|---|---|---|---|---|---|---|
| Am. Sul. PCPT[a] | 800 | 8000 | 0.41 | 4.1 | 1,951 | — | — |
| Chromatofocusing void volumes[b] | 200 | 600 | 0.0025 | .0075 | 80,000 | 41 | 3.75 |

[a]The crude bacteriocins produced by*Propionibacterium jensenii* P126 was obtained by ammonium sulfate precipitation of spent broth cultures of *Propionibacterium Jensenii* P126.
[b]This sample is the pooled void volumes from a chromatofocusing run at pH 9.0–6.0.

EXAMPLE 11

In order to further characterize the particular *P. jensenii* P126 bacteriocin, its isoelectric point was determined by bulk ion-exchange separation using a QAE Sephadex A-25 made by Pharmacia. The Sephadex was swollen and equilibrated for 24 hours with a 0.1 molar ethanolamine buffer. The pHs used were 9.0, 9.2, 9.4, 9.6, 9.8, 10.0, 10.5, 11.0, 11.5, and 12.0. After equilibration in the buffers, the excess buffer was drawn off and 5 ml of the bacteriocin was added. The pH was adjusted back to the pH at which the Sephadex had been equilibrated. The samples were then mixed gently for an hour and the Sephadex allowed to settle to the bottom of the beakers. The partially purified bacteriocin was removed and the pH adjusted back to 7.0. The samples were titered for activity and the protein content was determined. As a control, a sample of the crude bacteriocin was raised to a pH of 12.0 and held at this pH while the samples were being mixed with the ion exchanger. When the samples were adjusted to a pH of 7.0, the crude sample was also adjusted to a pH of 7.0 and assayed for activity and protein content. The crude bacteriocin retained much of its activity after being held at a pH of 12.0 for 1 hour. The activity of the control was 800 AU/ml. All samples having a pH of 11 and below exhibited the same activity as the crude bacteriocin. Samples at pHs of 11.5 and 12.0 exhibited an activity of 100 AU/ml. Accordingly, the isoelectric point was determined to be between 11.0 and 11.5.

EXAMPLE 12

A molecular weight estimation for the P126 bacteriocin was found by performing SDS-polyacrylimide gel electrophoresis (SDS-PAGE). After the partially purified post-chromatofocussed bacteriocin was run on the SDS-PAGE, the gels were stained with Coomassie blue and soaked in water overnight after destaining. The lanes that had been loaded with the partially purified bacteriocin were transferred to MRS agar plates along with the lanes that had been loaded with the molecular weight standards. The plates were overlaid with soft MRS agar that had been seeded with *L. delbrueckii* subsp. *lactis* ATCC 4797 and incubated to allow growth of the indicator. The indicator was inhibited only in the lanes that had been loaded with the partially purified bacteriocin. The corresponding band on the SDS-PAGE indicated that the approximate molecular weight of the bacteriocin was between 8,000 and 12,000 daltons.

EXAMPLE 13

The yogurt starter cultures, *Lactobacillus delbrueckii* subsp. *bulgaricus* strain PDY1 *bulgaricus*) and *Streptococcus salivarius* subsp. *thermophilus* strain CH3 (*S. thermophilus*) were tested separately for sensitivity to the P126 bacteriocin in broth media and in milk. The effects of jenseniin G in broth media were examined by adding the P126 bacteriocin produced according to Example 10 (80 AU/ml) to *L. bulgaricus* PDY1 and *S. thermophilus* CH3 cultures that had been grown in broth media for 9 hours at 37° C. Acidity, turbidity, and population in colony forming units (CFU) per ml were determined hourly for 9 hours, and again at 24 hours. The results indicated that the bacteriocin controls growth of both yogurt starter cultures. The acidity of cultures containing the bacteriocin remained lower than those without it. The turbidity of cultures containing the bacteriocin did not increase, thereby indicating no growth. The cultures without the bacteriocin retained a turbidity that is characteristic of the stationary growth phase. The population decreased by 99.9999%; the populations of cultures without the bacteriocin did not decrease.

EXAMPLE 14

The same yogurt starter bacteria (80 AU/ml) were added separately to skim milk containing the bacteriocin and acidity and populations were examined. The acidity of cultures with the bacteriocin remained lower than those without. The *S. thermophilus* with the bacteriocin remained approximately 0.35 pH units higher than without (control pH=4.4). The *L. bulgaricus* with the bacteriocin maintained a pH approximately 1.7 units higher than the control culture (control pH=3.8). FIG. 1 indicates the results of the acidity studies wherein "Lb PDY1" refers to *L. bulgaricus* control; "Lb PDY1+jG" refers to *L. bulgaricus* with P126 bacteriocin added; "St CH3" refers to *S. thermophilus* control; and "St CH3+jG" refers to *S. thermophilus* with P126 bacteriocin added.

The cultures died rapidly after adding the bacteriocin. The bacteriocin decreased the population of *S. thermophilus* by 99% and the population of *L. bulgaricus* by 99.9999%. Titers of the crude bacteriocin against strains of the Lactabacillus ranged from 800 to 3,200 AU/ml and activity against the streptococcal strains ranged from 100 to 400 AU/ml.

The sensitivity of *L. bulgaricus* and *S. thermophilus* to the bacteriocin indicates its ability to control excess acid formation in yogurt. Application of the bacteriocin to a lawn containing both cultures of lactabacillus and streptococcus yielded two distinct inhibition zones. Addition of the P126 bacteriocin to separate M17 broth cultures of streptococcus strains CH3, CR4, and PDY completely prevented their growth. Addition of the P126 bacteriocin to separate broth and skim milk cultures of streptococcal strain CH3 and lactobacillus strain PDY1 at a stationary phase had lethal effects on both cultures.

EXAMPLE 15

Bacteriocin from the *Propionibacterium jensenii* P1264 strain was prepared according to the method of Example 10 above by growing P1264 in NLA under flowing $CO_2$ at 30° C. for ten days. The bacteriocin culture was then centrifuged and filtered to remove cells but was not purified after being concentrated with ammonium sulfate.

EXAMPLE 16

The P1264 bacteriocin produced in Example 15 was then tested for inhibitory activity against *P. acidipropionici* P5, *P. jensenii* P126, *P. jensenii* P1264, *P. thoeni* P127, *Propionibacterium* subspecies P1262 and P1263, *L. delbrueckii* subsp. *lactis* ATCC 4797, *L. delbrueckii* ATCC 9649, *L. bulgaricus* NCDO 1489, *L. acidophilus* 6032, *L. casei* ATCC 7469, and *L. helveticus* ATCC 15009 by the deferred agar spot-on-lawn detection method as described in Example 1. The P1264 inhibited each of the bacteria tested.

EXAMPLE 17

The temperature and pH stability of the P1264 bacteriocin was tested according to the procedures described above and was found to be stable at pHs ranging from 0 to 13 and at temperatures of up to 100° C. for 45 minutes. The isoelectric point was determined as described above and was found to be approximately 6.5.

Further studies indicated that the bacteriocin was inactivated by treatment with pronase E and was unaffected by catalase. Treatment of the P1264 bacteriocin with pronase E potentiated the activity of the bacteriocin against propionibacteria and against *L. lactis* 4797 and expanded the inhibitory spectrum to *L. lactis* C2 and *L. plantarum* P1549 and 2901.

It should be understood that the present invention is not limited to the specific bacteria or processes described herein and that any bacteriocin equivalent to those described falls within the scope of the present invention. Preparation routes of the bacteriocins and process steps of inhibiting bacteria are merely exemplary so as to enable one of ordinary skill in the art to produce the bacteriocin and use it according to the described process and its equivalents.

It will also be understood that although the form of the invention shown and described herein constitutes a preferred embodiment of the invention, it is not intended to illustrate all possible forms of the invention. The words used are words of description rather than of limitation. Various changes and variations may be made to the present invention without departing from the spirit and scope of the following claims.

What is claimed is:

1. A process for inhibiting the growth of bacteria cultures of *Lactobacillus bulgaricus*, *Streptococcus thermophilus*, or mixtures thereof comprising adding to said bacteria cultures an effective amount of bacteriocins produced by *Propionibacterium jensenii* to inhibit the continued growth of said bacteria cultures.

2. The process as defined in claim 1 wherein said bacteria cultures are contained in yogurt.

3. The process as defined in claim 1 wherein said bacteriocins are produced by the ATCC 4872 strain of *Propionibacterium jensenii*.

4. A process for preventing the over-acidification of yogurt, said process comprising the step of adding bacteriocins produced by *Propionibacterium jensenii* to a yogurt, said yogurt containing a bacteria culture comprising *Lactobacillus bulgaricus* and *Streptococcus thermophilus*, and wherein said bacteriocins limit acid production within said yogurt by inhibiting further growth of said *Lactobacillus bulgaricus* and said *Streptococcus thermophilus*.

5. The process as described in claim 4, wherein said bacteriocins are produced by the ATCC 4872 strain of *Propionibacterium jensenii*.

6. The process as defined in claim 4, wherein said bacteriocins are added when said yogurt is at a pH below 6.0.

7. The process as defined in claim 6, wherein said pH is between about 4.5 to about 5.0.

8. The process as defined in claim 7, wherein said bacteriocins are added in an amount effective to prevent the pH of said yogurt from falling below about 4.0.

9. A process for inhibiting the growth of cultures of *Lactobacillus delbrueckii* subsp. *lactis*, *Lactobacillus helveticus*, or mixtures thereof, said process comprising the step of adding bacteriocins produced by the ATCC 4872 strain of *Propionibacterium jensenii* to said cultures, wherein said bacteriocins are added in an amount effective to inhibit the growth of said cultures.

10. A process for inhibiting the growth of a bacteria culture, said culture comprising bacteria selected from the group consisting of *Lactobacillus bulgaricus*, *Streptococcus thermophilus* and mixtures thereof, said process comprising the step of combining said bacteria culture with bacteriocins produced by the ATCC 4872 strain *Propionibacterium jensenii*, wherein said bacteriocins are present in an amount sufficient to inhibit further growth of said bacteria.

11. The process as defined in claim 10, wherein said bacteria culture is contained in a dairy product.

12. The process as defined in claim 11, wherein said dairy product is yogurt.

13. The process as defined in claim 12, wherein said bacteriocins inhibit said bacteria culture from producing acid within said yogurt by inhibiting the growth of said bacteria.

14. The process as defined in claim 12, wherein said bacteriocins are combined with said bacteria culture when said yogurt is at a pH of between about 4.5 and about 6.0.

15. The process as defined in claim 14, wherein said bacteriocins are present in an amount sufficient to prevent the pH of said yogurt from falling below 4.0.

* * * * *